(12) United States Patent
Sim et al.

(10) Patent No.: US 8,187,863 B2
(45) Date of Patent: May 29, 2012

(54) CELL-CHIP AND AUTOMATIC CONTROLLED SYSTEM CAPABLE OF DETECTING CONDITIONS FOR OPTIMIZING DIFFERENTIATION OF STEM CELL USING MECHANICAL STIMULUS

(75) Inventors: Woo Young Sim, Suwon (KR); Sang Sik Yang, Seoul (KR)

(73) Assignee: Ajou University Industry-Academic Cooperation Foundation, Gyeonggi-Do (KR)

( * ) Notice: Subject to any disclaimer, the term of this patent is extended or adjusted under 35 U.S.C. 154(b) by 327 days.

(21) Appl. No.: 12/438,103

(22) PCT Filed: Sep. 24, 2008

(86) PCT No.: PCT/KR2008/005673
§ 371 (c)(1),
(2), (4) Date: Feb. 19, 2009

(87) PCT Pub. No.: WO2009/107915
PCT Pub. Date: Sep. 3, 2009

(65) Prior Publication Data
US 2010/0233791 A1 Sep. 16, 2010

(30) Foreign Application Priority Data

Feb. 29, 2008 (KR) .................. 10-2008-0019136
Jul. 28, 2008 (KR) .................. 10-2008-0073300

(51) Int. Cl.
*C12M 1/36* (2006.01)
(52) U.S. Cl. ............... 435/286.4; 435/287.1; 435/288.5; 422/72
(58) Field of Classification Search ............... 435/286.4, 435/287.1; 422/72
See application file for complete search history.

(56) References Cited

U.S. PATENT DOCUMENTS

| | | | | |
|---|---|---|---|---|
| 5,858,804 A | * | 1/1999 | Zanzucchi et al. | 506/9 |
| 6,051,422 A | * | 4/2000 | Kovacs et al. | 435/287.1 |
| 2001/0029983 A1 | * | 10/2001 | Unger et al. | 137/597 |

(Continued)

FOREIGN PATENT DOCUMENTS

| KR | 10-0473362 A | 2/2005 |
|---|---|---|
| KR | 10-2006-0134264 A | 12/2006 |

OTHER PUBLICATIONS

Sim, Woo Young. "Microelectromechanical Devices for Stem Cell Stimulation and Detection". PhD thesis. Ajou University, Korea. pp. 68-86, Aug. 2007.*

(Continued)

*Primary Examiner* — William H Beisner
*Assistant Examiner* — Michael Hobbs
(74) *Attorney, Agent, or Firm* — Rabin & Berdo, P.C.

(57) ABSTRACT

Provided are a cell chip and a system thereof that are capable of detecting optimal conditions for stem cell differentiation by mechanical stimuli. The cell chip for cell differentiation experimentation includes a plurality of cell chambers for storing cells and culture media, cell and culture medium injection ports for transferring the cells and culture media to corresponding cell chambers, fine passages for moving the cells and the culture media injected into the cell and culture medium injection ports to the cell chambers, pneumatic injection ports for injecting pneumatic pressures applied to the cell chambers, and apertures having circular films for transferring the pneumatic pressures injected through the pneumatic injection ports to corresponding cell chambers. Here, at least two of the apertures may have different areas to vary the magnitude of pneumatic pressure applied to corresponding cell chambers.

7 Claims, 9 Drawing Sheets

U.S. PATENT DOCUMENTS

2002/0146822 A1* 10/2002 Takayama et al. ............ 435/375

OTHER PUBLICATIONS

Korean Intellectual Porperty Office for Application No. 10-2008-0073300. Jae Seung Yoon. Dated Jan. 31, 2010.*

Woo Young Sim et al. "Fabrication and Preliminary Test Results of a MEMS Cell Stimulator for Stem Cell Research.", IEEE International Conference on Nano/Micro Engineering and Molecular Systems, Zhuhai China, Jan. 18-21, 2006, pp. 1237-1240.

* cited by examiner

CELL-CHIP AND AUTOMATIC CONTROLLED SYSTEM CAPABLE OF DETECTING CONDITIONS FOR OPTIMIZING DIFFERENTIATION OF STEM CELL USING MECHANICAL STIMULUS

TECHNICAL FIELD

The present invention relates to a cell-chip capable of testing mechanical stimulus conditions for differentiating a stem cell, specifically, a mesenchymal stem cell, into bone and cartilage, and an automated cell-chip control system to which the cell chip can be detachably attached and used. More particularly, the present invention relates to a cell-chip and a control system thereof that are capable of rapidly and accurately detecting optimization conditions for stem cell differentiation by reflecting various experimental conditions in a single experiment.

BACKGROUND ART

With the advancement of research into proliferating and growing undifferentiated stem cells to obtain sufficient numbers of cells, various attempts have been tried to differentiate specific cells to regenerate and replace various injured tissues or organs. In particular, various methods have been advanced for developing adult stem cell differentiation technology which is free from ethical controversy and immune responses using undifferentiated stem cells like mesenchymal stem cells.

In specific differentiation environments, the mesenchymal stem cell in bone marrow has excellent proliferation ability and the potential to differentiate into various tissues such as bone, cartilage, muscle, fat, tendon, ligament, and nerve tissue. Bone/cartilage differentiation is the most advanced area of tissue engineering and differentiation research using stem cells.

In order to differentiate stem cells into bone/cartilage, biochemical differentiation induction methods have been used, in which the composition of culture medium is varied and/or different differentiation induction materials such as a transforming growth factor (TGF), a bone morphogenic protein (BMP), a fibroblast growth factor (FGF), an insulin-like growth factor (IGF), cytokines, and the likes are used. Recently, several research groups have begun to look at stem cell differentiation due to various mechanical factors such as shearing force applied by bodily fluids, compression force applied by various loads or external forces, tensile force, deformation force applied by external forces, elastic variation of an extracellular matrix, and so on.

While no theory about a precise pathway in a process of differentiating stem cells into bone/cartilage cells using mechanical stimulus has been established yet, recent research has revealed that after subjecting stem cells to various stimuli such as hydrostatic pressure, dynamic compression force, cell deformation, tension, hydraulic pressure and flow, electrodynamic force, convection, ultrasonic waves, and so on, protein synthesis and expression of bone/cartilage cell differentiation markers such as Sox9, collagen, GAGs and aggrecan increases, and expression of anti-differentiation factor IL-1 is suppressed.

Since conventional stem cell differentiation experiments using mechanical stimuli involve repeated culturing and differentiation of cells in petridishes, they are costly and laborious. That is, in order to observe variation of stem cells under various mechanical conditions, there is need of a large number of cells, repeated cell culturing, a new culture medium for each experiment, a large laboratory, and an expensive reagent and culture medium.

Therefore, in order to improve manual cell culturing and mechanical stimulus experiments, a new device and system employing various mechanisms and micromachining technologies are needed. In particular, a recently proposed pneumatic pressure-based cell-chip for a stem cell differentiation experiment using mechanical stimulus employs micro electro mechanical system (MEMS) technology to reduce probability of contamination, achieve an ultra-slim and lightweight structure, and enable visual observation using a transparent material.

However, conventional apparatuses for stem cell differentiation experiments using mechanical stimuli still require a separate experiment for each mechanical stimulus, which drives up costs and effort. In addition, they still require manual application of mechanical stimulus and change of culture medium to operate individual chips.

DISCLOSURE

Technical Problem

In order to solve the foregoing and/or other problems, it is an object of the present invention to provide a cell chip capable of simultaneously performing experiments with various mechanical stimuli to detect optimal conditions for stem cell differentiation.

In addition, it is another object of the present invention to provide a cell chip control system capable of automatically applying mechanical stimuli and changing a culture medium to detect optimal conditions for stem cell differentiation, and measuring magnitude of stimuli and differentiation steps of a stem cell using a pressure sensor integrated within each cell chip and a fluorescence microscope installed in the system in real time.

Technical Solution

To achieve the above objects, according to an aspect of the present invention, there is provided a cell chip for cell differentiation experimentation including: a plurality of cell chambers for storing cells and culture media; cell and culture medium injection ports for transferring the cells and culture media to corresponding cell chambers; fine passages for moving the cells and the culture media injected into the cell and culture medium injection ports to the cell chambers; pneumatic injection ports for injecting pneumatic pressures applied to the cell chambers; and apertures having circular films for transferring the pneumatic pressures injected through the pneumatic injection ports to corresponding cell chambers, wherein at least two of the apertures have different areas to vary the magnitude of pneumatic pressure applied to corresponding cell chambers.

Preferably, the plurality of cell chambers are disposed on a plurality of concentric circles about the pneumatic injection ports.

Preferably, the cell chip further includes a pressure sensor disposed at a lower surface of the cell chamber and sensing pressures of the cell chambers, wherein the lower surface of the cell chamber is a surface opposing a surface disposed in a direction from which pneumatic pressure is applied to the cell chambers.

Preferably, the pressure sensor may include first electrodes formed of indium tin oxide (ITO), disposed in the same arrangement as the cell chambers, and mounted on lower surfaces of the corresponding cell chambers; second electrodes formed of ITO and disposed opposite to corresponding first electrodes; and gap disposed between the first electrodes and second electrodes.

Preferably, the apertures may have different areas depending on distance from the pneumatic injection port of the corresponding cell chamber.

Preferably, the cell chip may further include a micro-valve device for adjusting fluid flow between the fine passages and the cell chambers. Here, the micro-valve device may include micro-valve pneumatic injection ports for injecting micro-valve pneumatic pressure; pneumatic chambers disposed to be in contact with the fine passages between corresponding cell chambers and contracting or expanding in response to the micro-valve pneumatic pressure; and a valve boss disposed between each corresponding cell chamber and fine passage and connected to a corresponding pneumatic chamber to be opened or closed in response to contraction or expansion of the corresponding pneumatic chamber.

Preferably, the cell chip may further include marker and dye injection ports for injecting a marker or dye to observe a cell state and a differentiation process in the cell chamber; and a fine passage connected between the marker and dye injection ports and acting as a moving passage of the marker or dye to the cell chamber. Here, the micro-valve device may include first micro-valve pneumatic injection ports for injecting first micro-valve pneumatic pressure used to adjust flow of a culture medium between the cell chamber and the fine passage; second micro-valve pneumatic injection ports for injecting second micro-valve pneumatic pressure used to adjust flow of a marker or dye between the cell chamber and the fine passage; first pneumatic chambers disposed to be in contact with the fine passage between corresponding cell chambers and contracting and expanding in response to the first micro-valve pneumatic pressure; second pneumatic chambers disposed to be in contact with each corresponding fine passage for a marker or dye and contracting and expanding in response to the second micro-valve pneumatic pressure; a first valve boss disposed between each corresponding cell chamber and fine passage and connected to a corresponding first pneumatic chamber to be opened or closed in response to contraction or expansion of the corresponding first pneumatic chamber; and a second valve boss disposed between each corresponding cell chamber and fine passage for a marker or dye and connected to a corresponding second pneumatic chamber to be opened or closed in response to contraction or expansion of the corresponding second pneumatic chamber.

According to another aspect of the present invention, there is provided a cell chip for cell differentiation experimentation including: an upper substrate formed of glass and including a pneumatic injection port through which a pneumatic pressure for applying a mechanical stimulus to a cell is injected, a cell and culture medium injection port through which a cell and a culture medium are injected, and a marker and dye injection port through which a marker or dye for visually observing a cell state is injected; a gasket disposed to be in contact with the upper substrate and forming an air chamber in which air introduced from the pneumatic injection port is stored; a polymer substrate including cell chambers for culturing cells, a first fine passage for moving a cell and a culture medium injected through the cell and culture medium injection port to the cell chambers, a second fine passage for moving the marker or dye injected through the marker and dye injection port to the cell chamber, and a micro-valve device for controlling fluid flow between the fine passages and the cell chambers; a multi-hole substrate disposed between the gasket and the polymer substrate, and having different areas to vary the magnitude of pneumatic pressure applied to corresponding cell chambers; a polymer thin film formed of an elastic polymer material and disposed between the multi-hole substrate and the polymer substrate to separate the air chamber and the cell chamber and apply pneumatic pressure to the cell chamber; a glass thin film having one surface in contact with the polymer substrate and another surface on which first electrodes are disposed at a lower part of the cell chamber to sense a pressure of the cell chamber; a lower substrate having second electrodes mounted on one surface opposite to corresponding first electrodes; and a support structure disposed between the glass thin film and the lower substrate and providing gap between the first and second electrodes.

According to still another aspect of the present invention, there is provided a cell chip control system for supplying pneumatic pressure, a cell, a culture medium, or the like, to a cell chip, and observing and measuring a state and differentiation of the cell in the cell chip.

Preferably, the cell chip control system may include an X-Y stage having a mounting part on which a cell chip is mounted, and moving or rotating the mounting part in a first direction in response to a first position signal; a Z stage moving in a second direction depending on a second position signal and connecting connection pipes for supplying pneumatic pressure, a cell, and a culture medium to the cell chip to an injection port corresponding to the cell chip; a pneumatic valve for varying magnitude and supply duration of pneumatic pressure supplied to a corresponding connection pipe in response to a first control signal; a syringe pump for providing a cell and a culture medium to the corresponding connection pipe in response to a second control signal; a measurement circuit for supplying a cell, a culture medium, and pneumatic pressure to the cell chip and measuring pressures of the cell chambers of the cell chip after an arbitrary time elapses; and a microcomputer for generating the first position signal, the second position signal, and the control signal, and receiving a measurement value from the measurement circuit to transfer the value to a user through an input/output device.

Preferably, the cell chip control system may further include a fluorescence microscope disposed at an upper part or a lower part of the mounting part and enabling visual observation of a cell in the cell chamber of the cell chip using a marker or dye.

Advantageous Effects

As can be seen from the foregoing, a cell chip and a control system thereof in accordance with exemplary embodiments of the present invention enable stem cell differentiation experiments under various stimulus conditions, such as application of mechanical stimuli having various magnitudes, periods, frequencies, intervals, and duty ratios, to be performed simultaneously in single pneumatic pressure. The cell chip and control system thus conserve stem cells and reduce experimentation time.

In addition, the present invention provides a cell chip and a control system thereof that are capable of automatically injecting and changing a cell and a culture medium using an integrated micro-valve system.

Further, magnitude of stimulus can be measured and cell differentiation steps can be observed in real time using a pressure sensor integrated within each cell chip and a fluorescent microscope installed in the system.

DESCRIPTION OF DRAWINGS

The above and other objects, features and advantages of the present invention will become more apparent from the following detailed description taken in conjunction with the accompanying drawings, in which.

MODES OF THE INVENTION

In order to fully understand operational advantages of the present invention and objects accomplished by the present invention, the reader should refer to the accompany drawings which depict exemplary embodiments of the present invention.

Exemplary embodiments of the present invention will now be described in detail with reference to the accompanying drawings. Like reference numerals designate like elements throughout the drawings and description.

Figure 1:
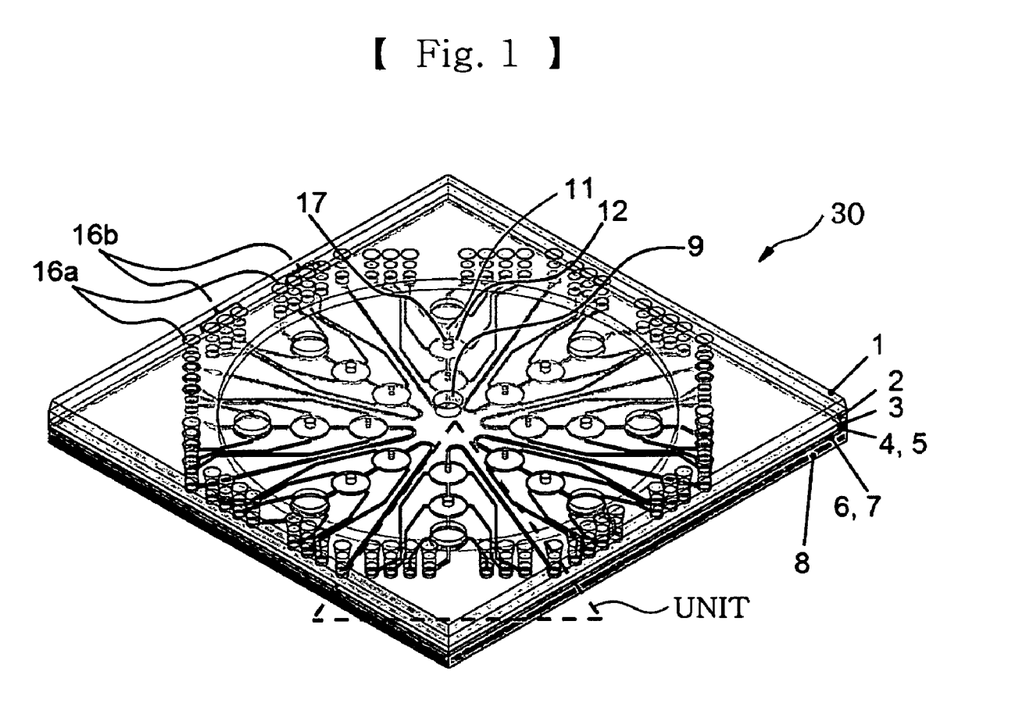
FIG. 1 is a perspective view of a cell chip in accordance with an exemplary embodiment of the present invention.

FIG. 1 is a perspective view of a cell chip in accordance with an exemplary embodiment of the present invention.

Referring to FIG. 1, a cell chip 30 in accordance with an exemplary embodiment of the present invention includes a pneumatic injection port 9, a cell and culture medium injection port 16a, a fine passage 11, and a cell chamber 12. The cell chip 30 in accordance with an exemplary embodiment of the present invention transfers a cell and a culture medium injected through the cell and culture medium injection port 16a into the cell chamber 12 through the fine passage 11, and applies a stimulus to a stem cell disposed in the cell chamber 12 through the pneumatic injection port 9 to detect differentiation conditions of the stem cell. In order to observe differentiation of the stem cell by the stimulus in the cell chamber, the cell chip 30 may further include a marker/dye injection port 16b through which a marker or dye is injected.

The cell chip 30 in accordance with an exemplary embodiment of the present invention includes a plurality of cell chambers. FIG. 1 shows the cell chip 30 having a structure in which twenty four cell chambers 12 having the same size and concentric distance from a center of the pneumatic injection port 9 are disposed. In addition, FIG. 1 shows the cell chip 30 having eight single units UNIT which each include three cell chambers 12 sharing fine passages 11.

However, the number of the cell chambers 12 included in the single unit UNIT is not limited. Depending on mechanical stimulus conditions and experimental environment, the number of cell chambers 12 may be different from that of the cell chip 30 of FIG. 1.

Different pressures may be applied to the three cell chambers included in the single unit UNIT. This can be implemented by varying the size of an aperture 17 for transferring air injected into the pneumatic injection port 9 to the cell chamber or a distance from the pneumatic injection port 9, as will be described below.

The cell chip 30 of FIG. 1 may comprise eight layers 1 to 8, and each layer may be formed of optically-observable, biocompatible glass or polymer. The polymer used in the cell chip 30 in accordance with an exemplary embodiment of the present invention may be typically polydimethylsiloxane (PDMS), polymethyl methacrylate (PMMA), polyimide, and so on.

Figure 2:
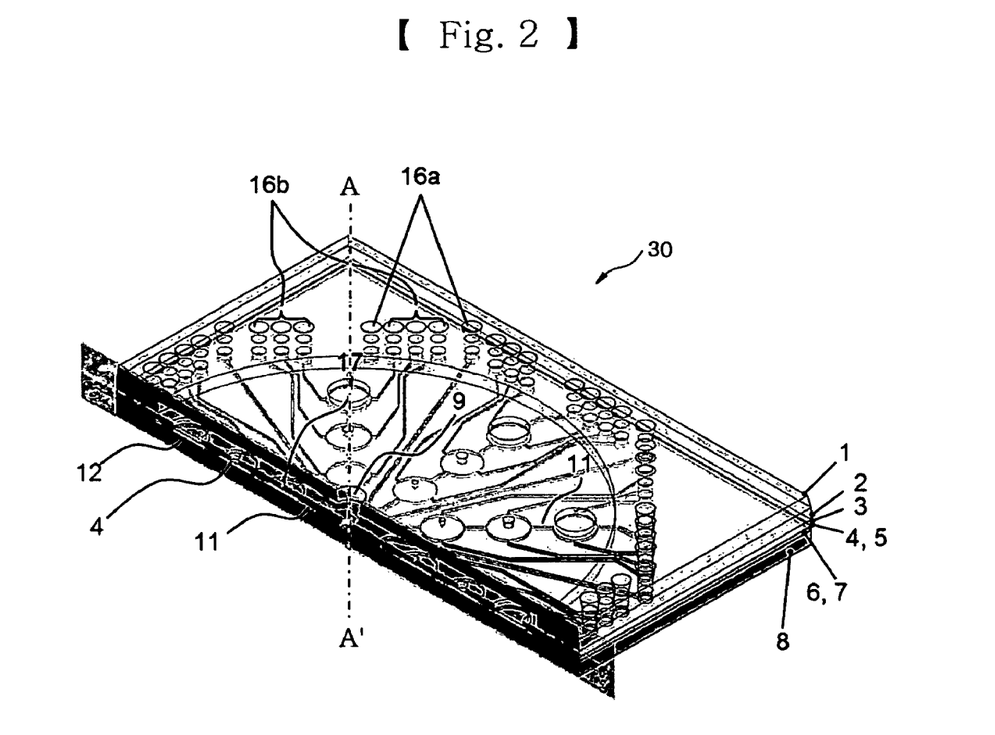
FIG. 2 is a perspective view of the cell chip of FIG. 1, a half of which is removed.
Figure 3:
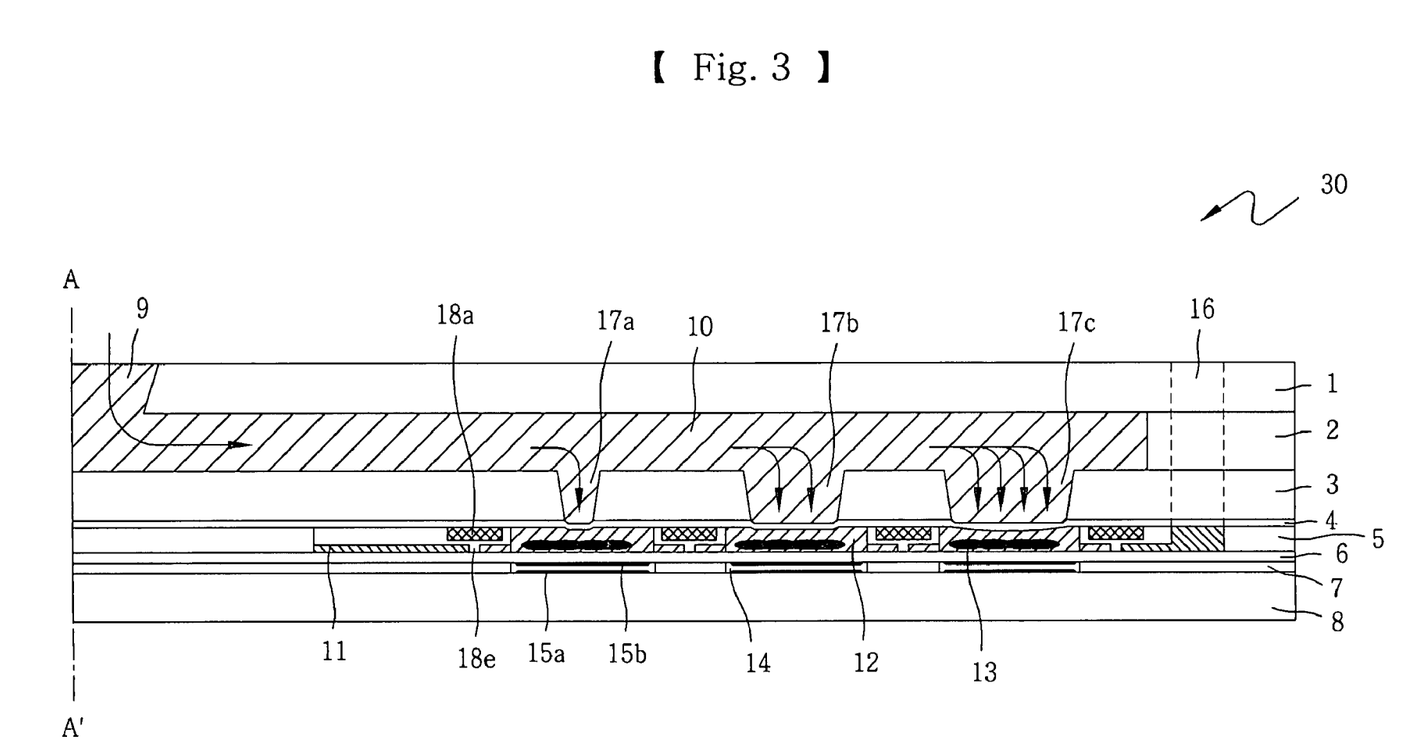
FIG. 3 is a cross-sectional view taken along line A-A' of FIG. 2.

FIG. 2 is a perspective view of the cell chip of FIG. 1, a half of which is removed, and FIG. 3 is a cross-sectional view taken along line A-A' of FIG. 2. Structures and functions of the layers of the cell chip 30 in accordance with an exemplary embodiment of the present invention will be described with reference to FIGS. 1, 2 and 3.

An upper substrate 1 including the pneumatic injection port 9 is formed of a glass material. The upper substrate 1 also acts as a cover of the cell chip 30.

A polymer gasket 2 has an air chamber 10 for storing air introduced from the pneumatic injection port 9 (along a solid arrow). In this invention, the gasket 2 of the cell chip 30 may be a polymer layer with several millimeters having a circular cavity such that a pneumatic pressure for stimulating a cell can uniformly propagate.

A multi-hole substrate 3 includes apertures 17 having different sizes to apply different pressures from a single pneumatic source 9 to different cell chambers 12. In particular, FIG. 3 shows apertures 17a, 17b and 17c for varying diameters thereof to generate a difference in an elastic force of the thin film 4 having a certain thickness to thereby apply different pressures to the cell chambers.

Here, in order to maximize a difference in mechanical stimulus conditions applied to the stem cell 13, unlike the apertures shown in FIG. 3, the aperture 17a near the pneumatic injection port 9 may have a larger diameter.

The polymer thin film 4 separates the air chamber 10 from the cell chamber. Here, the polymer thin film 4 may be formed of a flexible polymer material to apply a pressure to the cell chamber 12.

The polymer substrate 5 includes a cell chamber 12 as a space for culturing cells, a fine passage 11 for injecting a stem cell at the beginning of an experiment and periodically changing a culture medium, and a micro-valve (18a and 18e) system.

Figure 4:
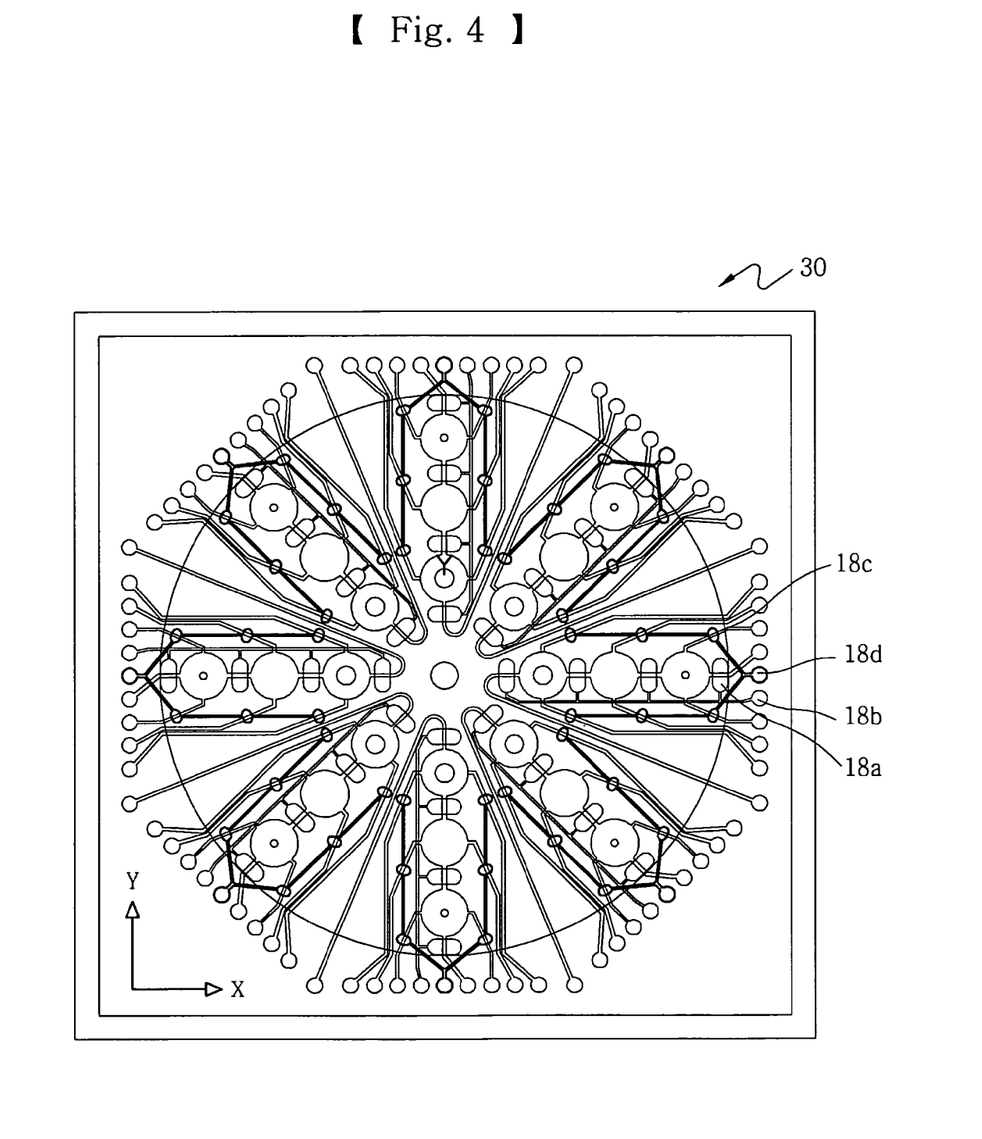
FIG. 4 is a plan view showing a micro-valve system for controlling fluid in a cell chip in accordance with an exemplary embodiment of the present invention.

FIG. 4 is a plan view showing a micro-valve system for controlling fluid in a cell chip in accordance with an exemplary embodiment of the present invention.

Referring to FIGS. 1 to 4, the micro-valve system included in the cell chip 30 in accordance with an exemplary embodiment of the present invention may include a micro-valve, which is always closed. Operation of the micro-valve system included in the cell chip 30 in accordance with an exemplary embodiment of the present invention will be described.

Upon injection of the cell or fluid, a back pressure (vacuum pressure) is applied to micro-valve pneumatic chambers 18a and 18c. In this case, the valve boss 18e blocking the fine passage 11 using the pneumatic chambers 18a and 18c for the contracted micro-valve is raised to allow fluid in the fine passage 11 to flow through the cell chamber 12.

Meanwhile, in an experiment applying mechanical stimuli to the stem cell, a pneumatic pressure is injected into the micro-valve chambers 18a and 18c to expand the micro-valve pneumatic chambers 18a and 18c. Therefore, while the pressure is applied to the cell chamber 12 to perform a stimulus experiment in a state in which the cell chamber 12 is closed, fluid flow between the fine passage 11 and the cell chamber 12 may be prevented by the expanded micro-valve pneumatic chambers 18a and 18c.

Here, the micro-valve pneumatic chambers 18a and 18c are classified into a first pneumatic chamber 18a for injecting a cell or a culture medium into the cell chamber 12, and a second pneumatic chamber 18c for injecting a marker or dye into the cell chamber 12. In addition, the micro-valve system in accordance with an exemplary embodiment of the present invention may separately include a first micro-valve pneumatic injection port 18b for applying pneumatic pressure or back pressure to the first pneumatic chamber 18a, and a second micro-valve pneumatic injection port 18d for applying pneumatic pressure or back pressure to the second pneumatic chamber 18c.

Next, structure and operation of the pressure sensor integrated within the cell chip 30 of the present invention to measure the pressure applied to the cell chamber 12 depending on the size of the aperture 17 will be described.

Referring to FIGS. 1, 2 and 3, the pressure sensor includes a glass thin film 6, a lower substrate 8, and a support structure 7 disposed between the glass thin film 6 and the lower substrate 8. One surface of the glass thin film 6 is in contact with the cell chamber 12, and the other surface includes an upper electrode 15b of the pressure sensor. A lower electrode 15a of the pressure sensor may be mounted on the lower substrate 8 as shown in FIG. 3.

The support structure 7 maintains an interval between the lower electrode 15a and the upper electrode 15b of several micrometers such that the pressure sensor can be operated. The gap between the pores 14 of the lower electrode 15a and the upper electrode 15b may vary according to the pressure applied to the cell chamber. Thus, capacitance of the sensing gap between the upper and lower electrodes may depend on the pressure of the cell chamber.

The electrodes of the pressure sensor in accordance with an exemplary embodiment of the present invention are transparent indium tin oxide electrodes and may have the same arrangement as the cell chambers 12. Use of transparent electrodes enables easy optical observation.

As described above, the cell chip in accordance with an exemplary embodiment of the present invention can apply mechanical stimuli of different magnitudes to the plurality of cell chambers in single pneumatic pressure to simultaneously perform stem cell differentiation experiments under various stimulus conditions. This conserves stem cells and reduces experimentation time. In addition, the cell chip in accordance with an exemplary embodiment of the present invention includes a pressure sensor integrated therewith as a single body to enable precise and convenient measurement of the pressure in the cell chamber applied depending on the size of the aperture.

Figure 5:
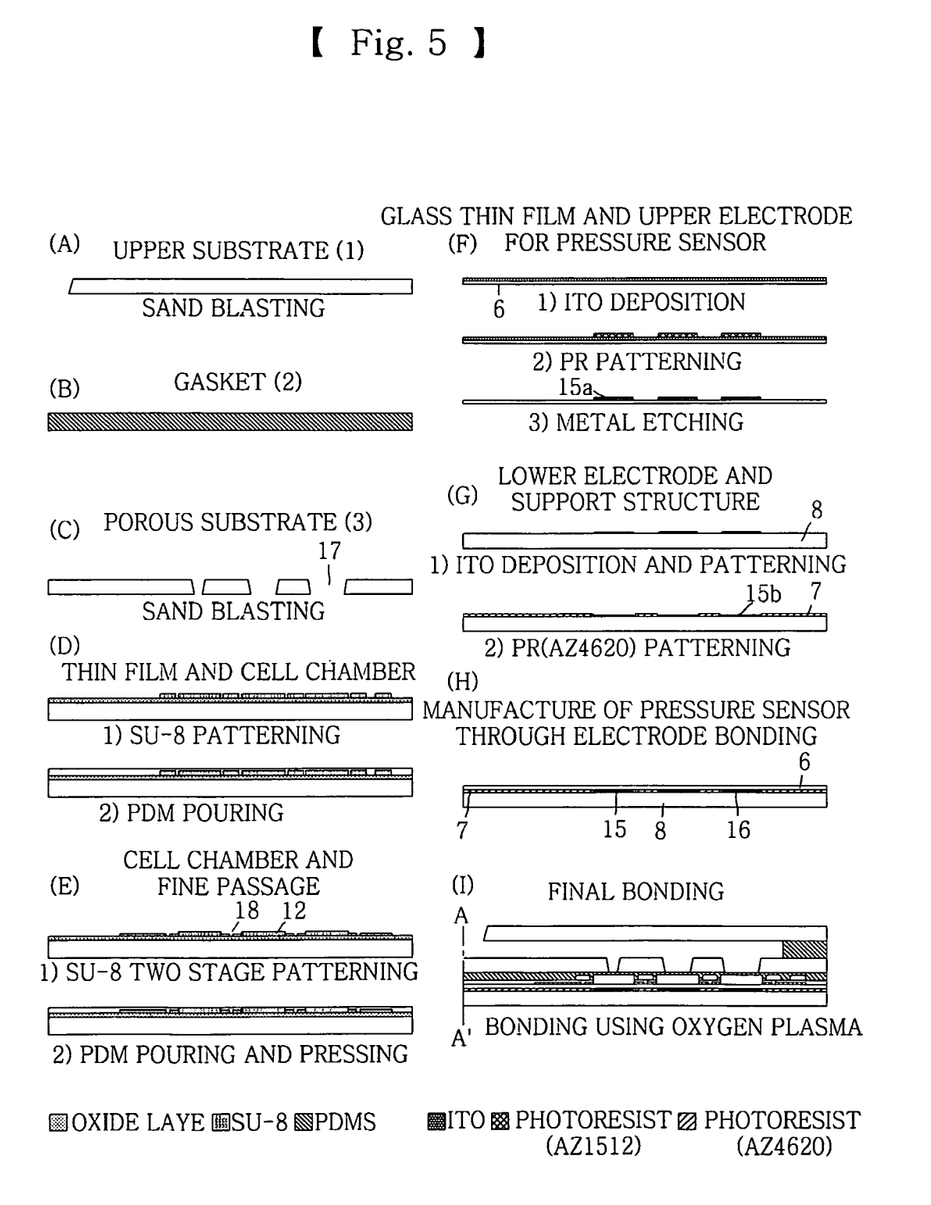
FIG. 5 shows cross-sectional views showing a manufacturing process of the cell chip of FIG. 1.

FIG. 5 shows cross-sectional views showing a manufacturing process of the cell chip of FIG. 1. Referring to FIGS. 1, 2, 3 and 5, a method of manufacturing a cell chip 30 in accordance with an exemplary embodiment of the present invention using a micro-machining process will be described.

The upper substrate 1 includes a pneumatic injection port 9, a cell and culture medium injection port 16a, a marker and dye injection port 16b, a first micro-valve pneumatic injection port 18b and a second micro-valve pneumatic injection port 18d. The multi-hole substrate 3 has various apertures 17. The upper substrate 1 and the multi-hole substrate 3 are manufactured by machining a glass substrate using a sand blasting method (see FIGS. 5 (a) and (c)).

The polymer substrate 5 including the gasket 2, the cell chamber 12, and the micro-valve system 18 may be manufactured through a PDMS standard molding process using a photoresist such as a thick negative photoresist (for example, SU-8, JSR, and so on), or a hot embossing process using PMMA (see FIGS. 5 (b), (d) and (e)).

The upper and lower electrodes 15b and 15a of the pressure sensor are manufactured by depositing transparent indium tin oxide (ITO) on the glass substrates 6 and 8 using a sputter, and patterning through photo-etching using a photoresist such as AZ1512 and metal-etching (see FIGS. 5(f) and (g)-1)). The support structure 7 is manufactured by spin coating and patterning using a photoresist (for example, AZ4620) appropriate to gap formation (see FIG. 5 (g)-2)). Next, the pressure sensor is manufactured through electrode bonding (see FIG. 5 (h)).

The layers manufactured as described above are surface-activated through oxygen plasma processing and then bonded to each other. After plasma bonding, the layers are baked in an oven at 75° C. for 24 hours to be permanently bonded to each other (see FIGS. 5 (i) and (j)). After bonding the all layers, side surfaces of the cell chip 30 are reinforced by adhesive such as epoxy, and then dried to strengthen adhesion of each layer, thereby preventing leakage of water and pneumatic pressure from poorly bonded parts.

The cell chip in accordance with an exemplary embodiment of the present invention is manufactured by alternately bonding a solid glass and a flexible polymer substrate to minimize deformation due to pneumatic pressure. Since the material and the manufacturing method used in the cell chip manufacturing process of FIG. 5 are well known by those skilled in the art, a description thereof will be omitted.

Figure 6:
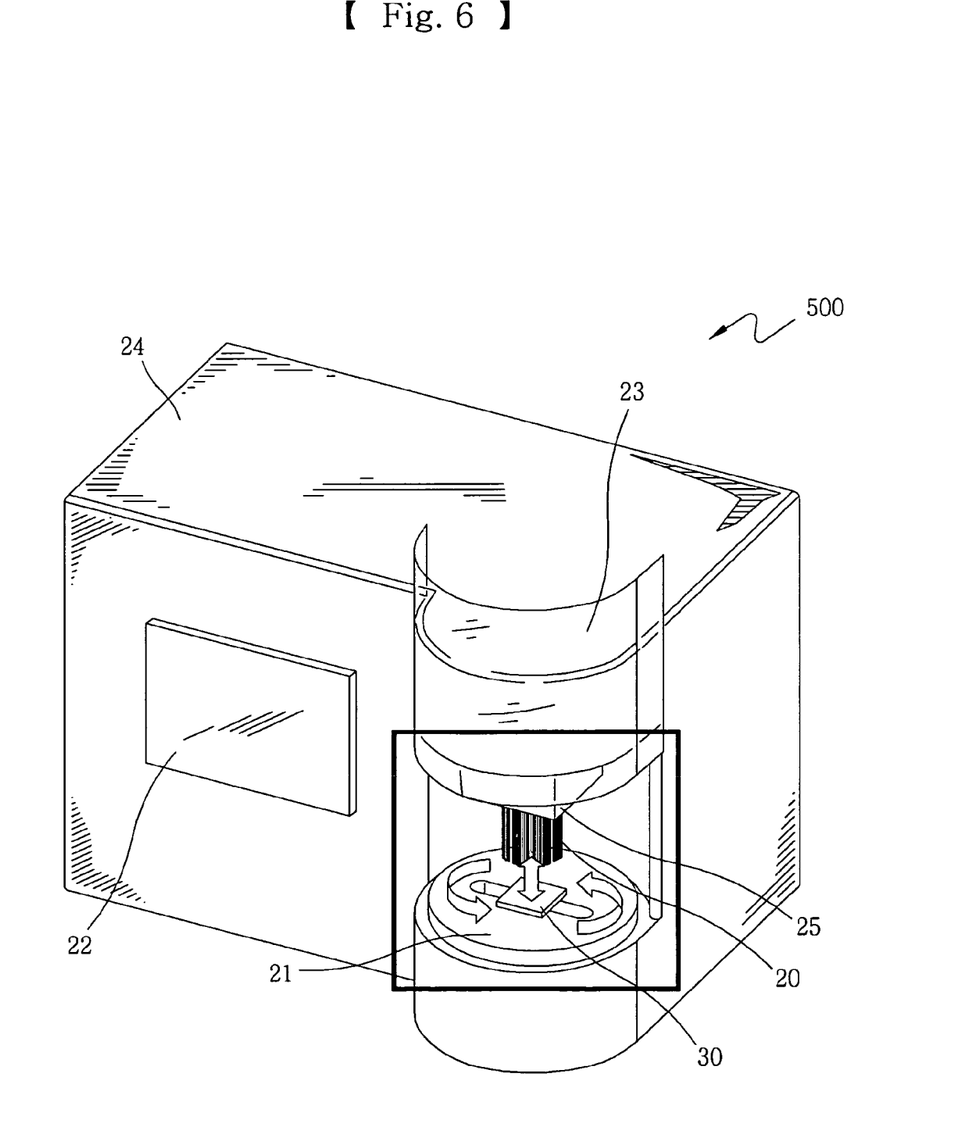
FIGS. 6 and 7 are a perspective view and an enlarged view of a cell chip control system in accordance with an exemplary embodiment of the present invention, in which the cell chip of FIG. 1 is detachably attached to automatically inject a cell, supply a culture medium, apply a mechanical stimulus, control a micro-valve system, and inject marker/dye.
Figure 7:
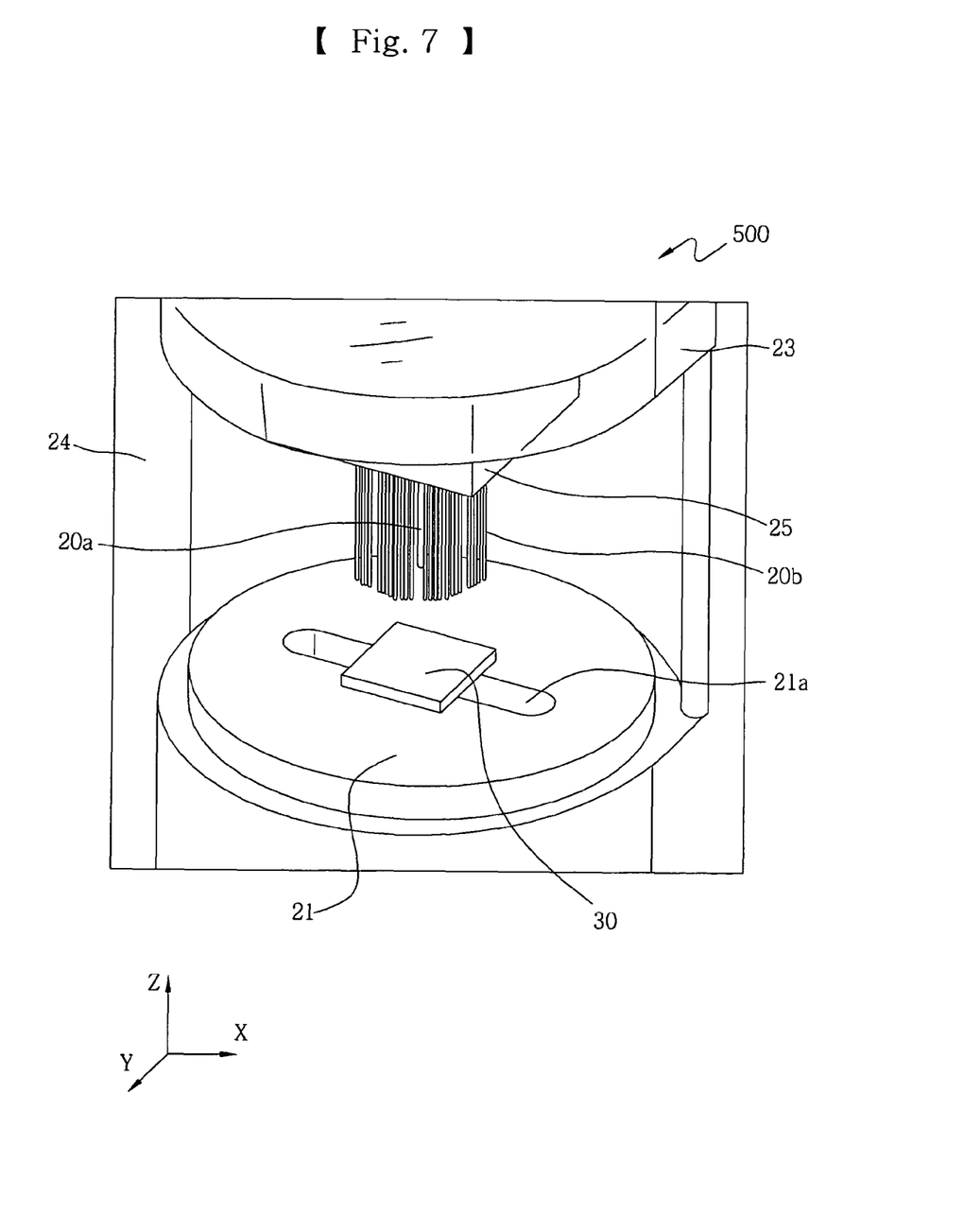
Figure 8:
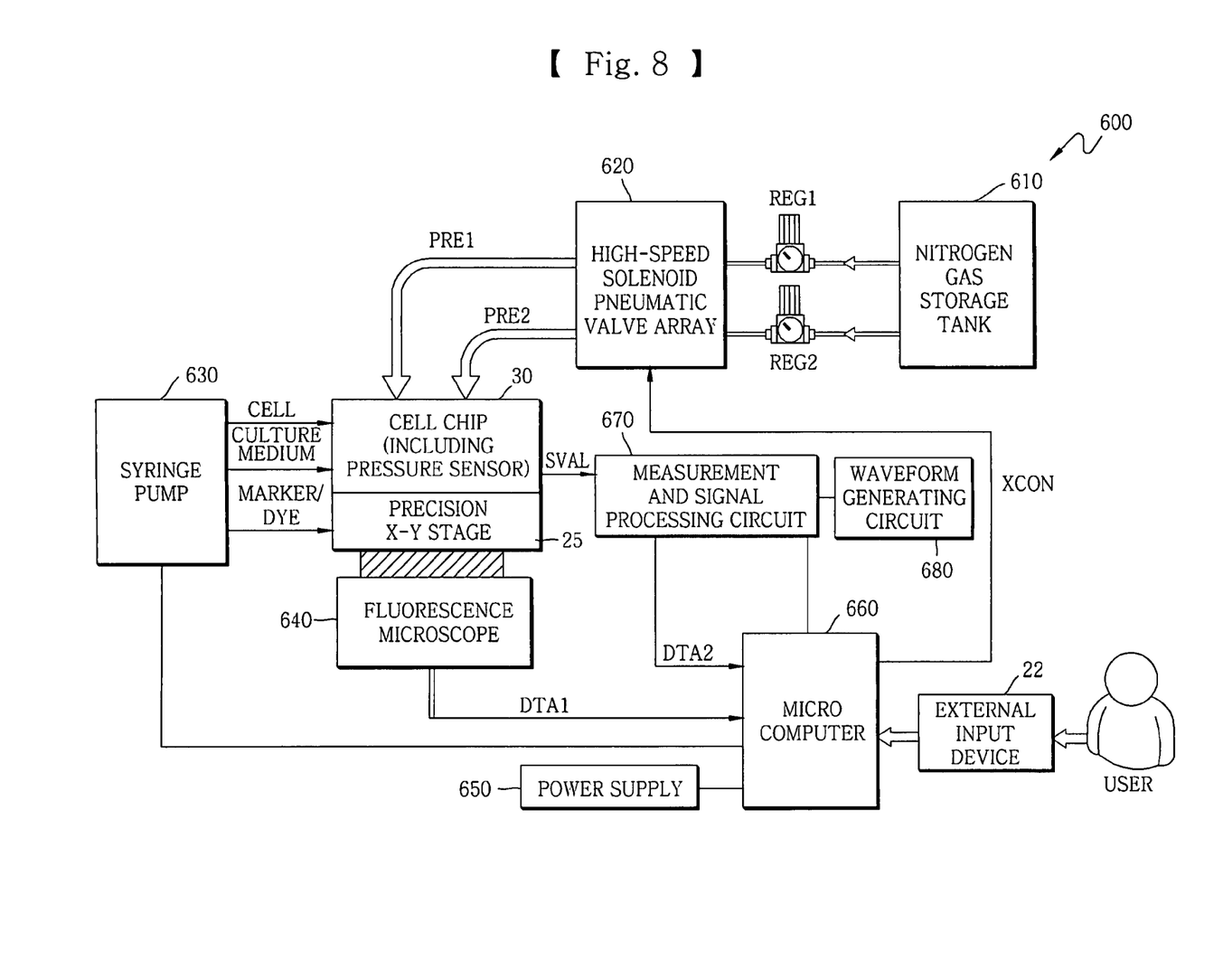
FIG. 8 is a block diagram showing an inner structure and operation of the system of FIGS. 6 and 7.

FIGS. 6 and 7 are a perspective view and an enlarged view of a cell chip control system in accordance with an exemplary embodiment of the present invention, in which the cell chip of FIG. 1 is detachably attached to automatically inject a cell, supply a culture medium, apply a mechanical stimulus, control a micro-valve system, and inject a marker/dye. FIG. 8 is a block diagram showing an inner structure and operation of the system of FIGS. 6 and 7. Referring to FIGS. 6, 7 and 8, structure and operation of the cell chip control system 500 in accordance with an exemplary embodiment of the present invention will be described.

First, the cell chip 30 of FIG. 1 is mounted on a mounting part 21a. The mounted cell chip 30 is located at an initial position which is already programmed in an X-Y stage 21 that can move or rotate the mounting part 21a in an X-Y axis direction (see FIG. 4). The initial position, where the cell chip is mounted, should be precisely set for coupling of several tens of connection pipes to an ultra-small cell chip and for observation of the state of cells in a plurality of cell chambers.

When the cell chip 30 is mounted, in order to minimize contamination or infection from the exterior, a transparent sliding cover 23 may be lowered to hermetically seal off the cell chip 30 from the exterior.

Over the mounted cell chip 30, a connection pipe 20b for supplying a cell and a culture medium or operating a micro-valve system, and a connection pipe 20a for providing pneumatic pressure to the cell move in a Z-axis direction through a Z-axis stage to be connected to the injection ports 9, 16a, 18b and 18d (see FIGS. 1 to 4) of the cell chip 30.

Next, when a back pressure (a vacuum) is applied to the first micro-valve pneumatic injection port 18b, the valve boss 18e (see FIG. 3) blocking the cell chamber 12 is opened, and the stem cell 12 (see FIG. 3) mixed with the culture medium is injected by a syringe pump 630. Then, the state of the cell chip is maintained as described above for a certain time such that the stem cell settles on the bottom of the cell chamber 12.

It was found experimentally that the stem cell injected into the cell chamber settles on the bottom after about 12 hours.

After checking whether the cell has settled, desired mechanical stimulus magnitude, interval, frequency, period, and duty ratio can be input through a touch screen 22. As shown in FIG. 8, a microcomputer 660 transfers a control signal XCON to a high-speed solenoid pneumatic valve 620 depending on an input value. The solenoid pneumatic valve 620 performs ON/OFF operations in response to the control signal XCON such that a user can apply pneumatic pressure having a desired period, interval, frequency, and duty ratio to the air chamber 10 of the cell chip 30.

At this time, pneumatic pressure PRE1 for a mechanical stimulus and pneumatic pressure PRE2 for a micro-valve may be provided to a solenoid pneumatic valve 620 by regulating nitrogen gas discharged from a nitrogen gas storage tank 610 using a corresponding regulator REG1 or REG2 (for example, depressurizing the nitrogen gas).

Components of FIG. 8 may be installed in a frame 24 of FIG. 6. However, several components such as the nitrogen gas storage tank 610 may be installed at the exterior of the frame 24 due to their bulky size.

When the pneumatic pressure is transferred to the cell chip as described above, the pressure sensor senses the pressure of the corresponding cell chamber, and the measurement and signal processing circuit 670 receives and converts the measured valve into a digital valve to transfer it to the microcomputer 660. The microcomputer 660 can output the pressure of each cell chamber to the touch screen 22.

Figure 9:
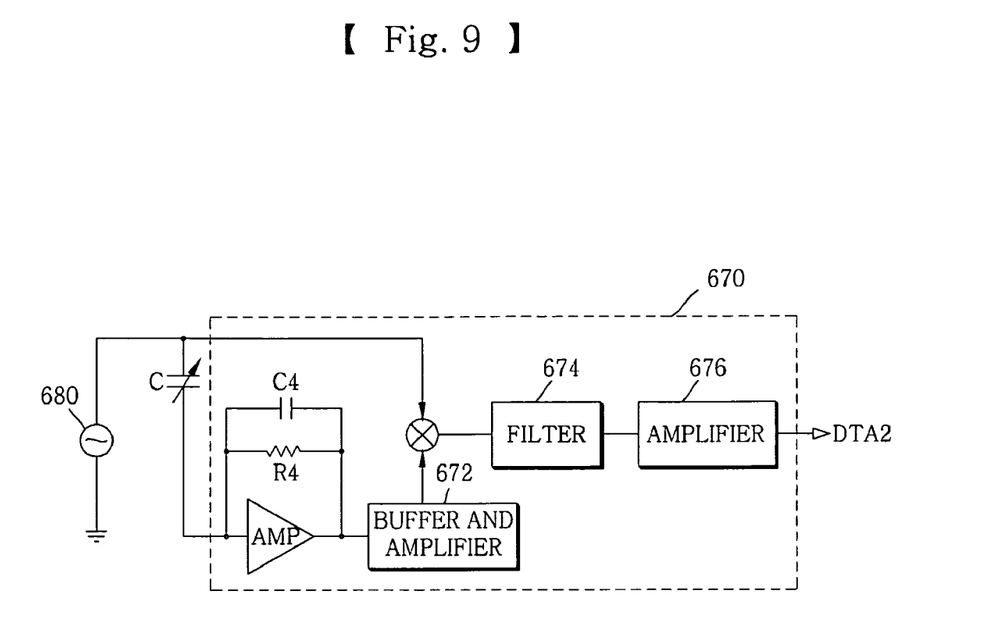
FIG. 9 is a view showing a structure and operation of a measurement and signal processing circuit of FIG. 8.

FIG. 9 is a view showing a structure and operation of a measurement and signal processing circuit of FIG. 8.

Referring to FIGS. 8 and 9, capacitance of a variable capacitor formed of the upper and lower electrodes of the pressure sensor may be referred as to C. A charge coupler AMP of FIG. 9 converts variation in the capacitance C into variation in voltage. At this time, conversion sensitivity depends on capacitance Cf of a feedback capacitor. When the magnitude of Cf is smaller than a variation amount of C, since the capacitor may be readily saturated and cannot be appropriately used, a capacitor having tens to hundreds of times larger capacitance than the variation amount of C may be generally selected and used. A feedback resistance Rf makes a bias current and is higher than a sensor impedance at low frequency.

When the variation in capacitance is converted into a voltage, since the signal is very small, a buffer/amplifier 672 functions to amplify the signal. A carrier wave and the converted measurement signal are overlapped in a multiplier 678 to be offset to remain a variation value, finally detecting a required signal only through a filter 674 and an amplifier 676.

However, since the electrodes 15a and 15b (see FIG. 3) of the pressure sensor have a diameter of several millimeters and variation in capacitance due to fine variation in pressure of the cell chamber is lower than several to several tens of femtofarad fF, a signal SVAL sensed by the pressure sensor is very sensitive to noise. Therefore, the present invention performs amplitude modulation (AM) and demodulation using a carrier signal, filtering through the filter 674, and amplification through the amplifier 676, to minimize noise and precisely detect a measurement value DTA2 of the pressure in the cell chamber. Here, the carrier signal may be provided by a waveform generating circuit 680.

Referring back to FIG. 8, the cell chip control system in accordance with an exemplary embodiment of the present invention can perform a stimulus experiment for one week to one month and store cell propagation and differentiation images daily or weekly. If necessary, differentiation of the cell may be observed by opening or closing an individual micro-valve of each cell chamber and then injecting a fluorescent marker such as CD90, CD105, CD29 or actin and a dye such as alkaline phosphatase (ALP) or Alizarin red for dying Ca, a characteristic ingredient for bone differentiation, using a syringe pump.

A cell state and variation in the cell chip 30 can be observed using a microscope 640 mounted on a lower part of the X-Y stage 21 of FIG. 6. In order to observe the cell state of each cell chamber at each time, the X-Y stage 21 can move the cell chip to an X-Y position programmed by the microcomputer 660 and precisely rotate the cell chip by a certain angle to observe the cell at concentric angular intervals.

Experimental data DTA1 observed through the fluorescence microscope 640 can be transferred to the microcomputer 660. As described above, the microcomputer 660 can perform various experimental controls, display experimental results through an external display device 22, or receive experimental conditions and so on from a user. The microcomputer 660 can receive power from a power source 650 and operate.

A user can analyze pressures measured during the experiment and image data of cell differentiation to determine correlation between the magnitude of a mechanical stimulus, interval, frequency, period, duty ratio, bone differentiation of a stem cell, and calcium generation, thereby finding optimal stimulus conditions.

While this invention has been described with reference to exemplary embodiments thereof, it will be clear to those of ordinary skill in the art to which the invention pertains that various modifications may be made to the described embodiments without departing from the spirit and scope of the invention as defined in the appended claims and their equivalents.

The invention claimed is:

1. A cell chip for cell differentiation experimentation of stem cell, comprising:
    a plurality of cell chambers for storing cells and culture media;
    cell and culture medium injection ports for transferring the cells and culture media to corresponding cell chambers;
    first fine passages for moving the cells and the culture media injected into the cell and culture medium injection ports to the cell chambers;
    a pneumatic injection port for injecting pneumatic pressures applied to the cell chambers;
    apertures having circular films for transferring the pneumatic pressures injected through the pneumatic injection ports to corresponding cell chambers;
    marker and dye injection ports for injecting a marker or dye to observe a cell state and a differentiation process in the cell chamber;
    second fine passages connected between the marker and dye injection ports and acting as a moving passage of a marker or dye to the cell chamber; and
    a micro-valve device for adjusting fluid flow between the fine passage and the cell chamber, fluid flow between the passage and the cell chamber, and fluid flow between two adjacent cell chamber,
    wherein:
    at least two of the apertures have different areas to vary the magnitude of pneumatic pressure applied to corresponding cell chambers;
    the plurality of cell chambers are disposed on a plurality of concentric circles about the pneumatic injection port, at least two cell chambers being disposed on a same circle about a center of the pneumatic injection port, the plurality of cell chambers are divided into a plurality of units, each unit consisting of a number of cell chambers, between two adjacent ones of which the first fine passages are disposed; and the micro-valve device comprises:

first micro-valve pneumatic injection ports for injecting first micro-valve pneumatic pressure used to adjust flow between the cell chamber and the first fine passage and to adjust flow between two adjacent ones of the cell chambers in each unit;

second micro-valve pneumatic injection ports for injecting second micro-valve pneumatic pressure used to adjust flow of a marker or dye between the cell chamber and the second fine passage;

first pneumatic chambers disposed to be in contact with the first fine passage between corresponding cell chambers and contracting and expanding in response to the first micro-valve pneumatic pressure;

second pneumatic chambers disposed to be in contact with each corresponding second fine passage for a marker or dye and contracting and expanding in response to the second micro-valve pneumatic pressure;

a first valve boss disposed between each corresponding cell chamber and first fine passage and connected to a corresponding first pneumatic chamber to be opened or closed in response to contraction or expansion of the corresponding first pneumatic chamber, wherein flow between two adjacent ones of the cell chambers in each unit is blocked when the first valve boss is closed; and a second valve boss disposed between each corresponding cell chamber and second fine passage for a marker or dye and connected to a corresponding second pneumatic chamber to be opened or closed in response to contraction or expansion of the corresponding second pneumatic chamber.

2. The cell chip according to claim 1, further comprising:
a pressure sensor disposed at a lower surface of the cell chamber and sensing pressures of the cell chambers, wherein the lower surface of the cell chamber is a surface opposing a surface disposed in a direction from which pneumatic pressure is applied to the cell chambers.

3. The cell chip according to claim 2, wherein the pressure sensor comprises:

first electrodes formed of indium tin oxide (ITO), disposed in the same arrangement as the cell chambers, and mounted on lower surfaces of the corresponding cell chambers;

second electrodes formed of ITO and disposed opposite to the corresponding first electrodes; and gap disposed between the first electrodes and second electrodes.

4. The cell chip according to claim 1,
wherein the apertures have different areas according to distance from the pneumatic injection port of the corresponding cell chamber.

5. A cell chip control system, on which a cell chip according to claim 1 is mounted, for supplying pneumatic pressure, a cell, or a culture medium to the cell chip, and observing and measuring a state and differentiation of the cell in the cell chip.

6. The cell chip control system according to claim 5, comprising:

an X-Y stage having a mounting part on which a cell chip is mounted, and moving or rotating the mounting part in a first direction in response to a first position signal;

a Z stage moving in a second direction depending on a second position signal and connecting connection pipes for supplying pneumatic pressure, a cell, and a culture medium to the cell chip to an injection port corresponding to the cell chip;

a pneumatic valve for varying magnitude and supply duration of pneumatic pressure supplied to a corresponding connection pipe in response to a first control signal;

a syringe pump for providing a cell and a culture medium to the corresponding connection pipe in response to a second control signal;

a measurement circuit for supplying a cell, a culture medium, and pneumatic pressure to the cell chip and measuring pressures of the cell chambers of the cell chip after an arbitrary time elapses; and a microcomputer for generating the first position signal, the second position signal, and the control signal, and receiving a measurement value from the measurement circuit to transfer the value to a user through an input/output device.

7. The cell chip control system according to claim 6, further comprising:

a fluorescence microscope disposed at an upper part or a lower part of the mounting part and enabling visual observation of a cell in the cell chamber of the cell chip using a marker or dye.

* * * * *